United States Patent [19]
Yan

[11] Patent Number: 5,476,983
[45] Date of Patent: Dec. 19, 1995

[54] RECLAMATION OF HF AND RECOVERY OF GASOLINE FROM ACID-SOLUBLE OIL BY CRACKING

[75] Inventor: Tsoung Y. Yan, Philadelphia, Pa.

[73] Assignee: Mobil Oil Corporation, Fairfax, Va.

[21] Appl. No.: 285,674

[22] Filed: Aug. 4, 1994

[51] Int. Cl.$^6$ .................................................. C07C 2/62
[52] U.S. Cl. .................. 585/719; 585/723; 585/724; 585/730; 585/802
[58] Field of Search .................................. 585/719, 723, 585/724, 730, 802

[56] References Cited

U.S. PATENT DOCUMENTS

| | | | |
|---|---|---|---|
| 3,793,264 | 2/1974 | Chapman | 585/724 |
| 5,191,150 | 3/1993 | Child et al. | 585/809 |
| 5,264,650 | 11/1993 | Better et al. | 585/802 |
| 5,264,651 | 11/1993 | Better et al. | 585/802 |
| 5,264,652 | 11/1993 | Child et al. | 585/802 |
| 5,276,243 | 1/1994 | Better et al. | 585/802 |

*Primary Examiner*—Asok Pal
*Attorney, Agent, or Firm*—Alexander J. McKillop; Dennis P. Santini; Robert B. Furr, Jr.

[57] ABSTRACT

The present invention provides a method for reclaiming HF and producing valuable gasoline blending components from the conjunct polymeric byproducts (acid soluble oil or ASO) formed as a byproduct of acid-catalyzed isoparaffin-olefin alkylation comprising the steps of:

(a) reacting isoparaffin and olefin in the presence of a liquid acid alkylation catalyst to form alkylate and ASO byproduct;

(b) separating alkylate, unreacted isoparaffin, and a majority of said liquid acid alkylation catalyst from said ASO;

(c) reacting said separated ASO of step (b) under conditions of elevated temperature and pressure to convert the hydrocarbon portion of said ASO to gasoline boiling range hydrocarbons and to liberate HF.

In a preferred embodiment, the ASO is pre-mixed with hydrogen or a hydrogen donor before reaction at elevated temperature and pressure. In a particularly preferred embodiment, the elevated temperature reaction is carried out in the presence of a catalyst such as activated carbon.

18 Claims, 1 Drawing Sheet

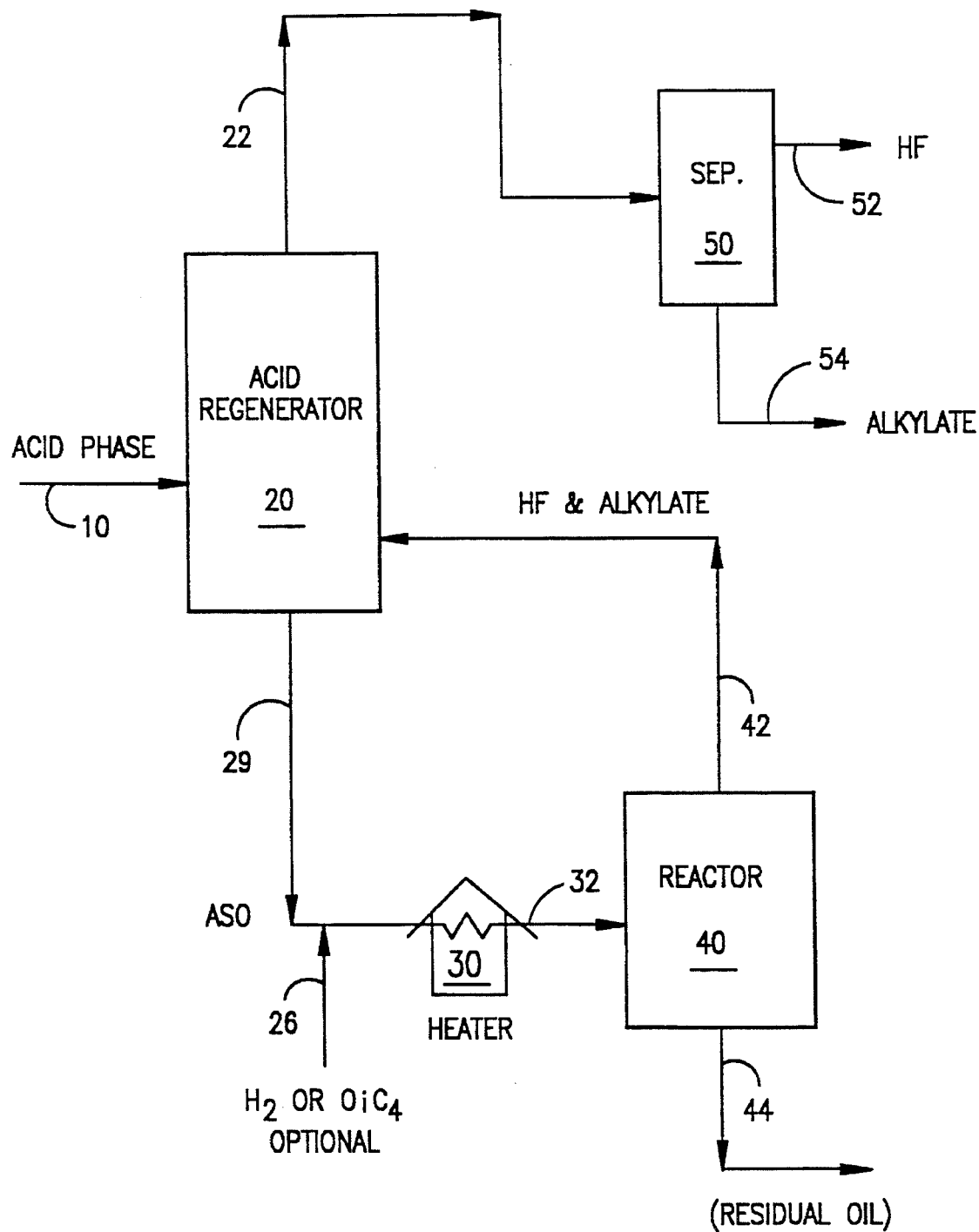

RECLAMATION OF HF AND RECOVERY OF GASOLINE FROM ACID-SOLUBLE OIL BY CRACKING

FIELD OF THE INVENTION

The present invention relates to the art of catalytic alkylation. More specifically, the invention relates to a liquid alkylation catalyst and an isoparaffin-olefin alkylation process. Particularly, the invention provides a method for reclaiming HF and recovering valuable gasoline blending components from acid-soluble oil (ASO).

BACKGROUND OF THE INVENTION

Alkylation is a reaction in which an alkyl group is added to an organic molecule. Thus an isoparaffin can be reacted with an olefin to provide an isoparaffin of higher molecular weight. Industrially, the concept depends on the reaction of a $C_2$ to $C_5$ olefin with isobutane in the presence of an acidic catalyst producing a so-called alkylate. This alkylate is a valuable blending component in the manufacture of gasolines due its high octane rating, low vapor pressure, and susceptibility to octane-enhancing additives.

Industrial alkylation processes have historically used concentrated hydrofluoric or sulfuric acid catalysts under relatively low temperature conditions. Acid strength is preferably maintained at 85 to 94 weight percent by the continuous addition of fresh acid and the continuous withdrawal of spent acid. As used herein, the term "concentrated hydrofluoric acid" refers to an essentially anhydrous liquid containing at least about 85 weight percent HF. For commercial catalytic isoparaffin-alkylation, the HF catalyst typically contains from about 1 to about 2 weight percent water to enhance activity.

Hydrofluoric and sulfuric acid alkylation processes share inherent drawbacks including environmental and safety concerns, acid consumption, and sludge disposal. For a general discussion of sulfuric acid alkylation, see the series of three articles by L. F. Albright et al., "Alkylation of Isobutane with $C_4$ Olefins" 27 *Ind. Eng. Chem. Res.*, 381–397, (1988). For a survey of hydrofluoric acid catalyzed alkylation, see 1 *Handbook of Petroleum Refining Processes* 23–28 (R. A. Meyers, ed., 1986).

Isoparaffin-olefin alkylation processes typically convert at least a portion of the feedstock to conjunct polymeric byproducts, which are more commonly referred to as acid soluble oil or ASO. In a typical HF-catalyzed isoparaffin-olefin alkylation process, the acid catalyst is partially withdrawn and regenerated by stripping using hot i-butane. Since the acid phase dissolves some polymer oil, the heavy bottom product, acid soluble oil (ASO) is obtained in the acid regenerator. This bottom product is generally known as ASO or polymer/constant boiling mixture (CBM). The ASO is charged to a hot storage tank, where phase separation takes place. The top layer is oil which can contain fluorine and is sent to a catalytic cracker or a coker as feedstock to recover the hydrocarbons. The bottom phase is HF acid and water which is neutralized with caustics such as NaOH and KOH and finally limed to make $CaF_2$ precipitate for disposal. The treatment of ASO for disposal is costly, converting valuable HF into $CaF_2$ for costly disposal, while downgrading the hydrocarbon portion of the ASO to a feedstock.

U.S. Pat. Nos. 5,264,650, 5,264,651, 5,264,652, 5,276,243, and 5,191,150 teach sulfolane recovery methods which involve reducing the HF concentration in a mixture of HF, sulfolane, and ASO to less than about 30 weight percent and then gravitationally separating the resulting for a mixture to recover sulfolane. The HF-enriched stream evolved from the stripping step of these processes contains a minor amount of relatively low boiling range conjunct polymeric byproducts (also referred to as "light acid soluble oil" or "light ASO") which is recycled to the alkylation reaction zone.

SUMMARY OF THE INVENTION

The present invention provides a method for reclaiming HF and producing valuable gasoline blending components from the conjunct polymeric byproducts (acid soluble oil or ASO) formed as a byproduct of acid-catalyzed isoparaffin-olefin alkylation.

In a first embodiment, the method of the invention includes the steps of:

(a) reacting isoparaffin and olefin in the presence of a liquid acid alkylation catalyst to form alkylate and ASO byproduct;

(b) separating alkylate, unreacted isoparaffin, and a majority of said liquid acid alkylation catalyst from said ASO;

(c) reacting said separated ASO of step (b) under conditions of elevated temperature and pressure to convert the hydrocarbon portion of said ASO to gasoline boiling range hydrocarbons and to liberate HF.

In a second embodiment, the method of the invention includes the steps of:

(a) reacting isoparaffin and olefin in the presence of a liquid acid alkylation catalyst to form alkylate and ASO byproduct;

(b) separating alkylate, unreacted isoparaffin, and a majority of said liquid acid alkylation catalyst from said ASO;

(c) mixing said ASO with a sufficient amount of hydrogen or a hydrogen donor to inhibit the reaction of ASO to coke at the elevated reaction temperature of step (d);

(d) reacting said mixture of step (c) under conditions of elevated temperature and pressure to convert the hydrocarbon portion of said ASO to gasoline boiling range hydrocarbons and to liberate HF.

In a preferred embodiment, the ASO is reacted in the presence of a catalyst, and active carbon is a particularly preferred catalyst support.

The conjunct polymeric byproducts of liquid acid catalyzed isoparaffin-olefin alkylation are understood to comprise a complex mixture, but the mechanism underlying the present invention is not well understood. The exact nature of the ASO is not known and it should vary somewhat with the nature of the alkylation feed and the operation condition of the alkylation unit. The ASO principally contains polymers of dienes formed in the isoparaffin-olefin alkylation reaction, together with other $C_{10}$–$C_{20}$ hydrocarbons. These hydrocarbons include highly branched paraffins and naphthenes but can also contain olefin bonds and fluorine. In addition to the fluorine contained in these compounds, ASO contains significant amounts of HF in the form of stable HF/hydrocarbon complexes.

The process of this invention reclaims valuable gasoline and HF from ASO by reacting the ASO mixture at temperatures of from about 200 to about 400° C. and total pressures of from about 10 to about 1000 psig in a reaction zone in a reaction zone at liquid hourly space velocity (LHSV) of from about 0.1 to about 100 $hr^{-1}$. The reaction products, predominately hydrocarbons which boil in the gasoline range, may be used as blending stock for high-octane gasoline. HF produced by the reaction is recycled to the isoparaffin-olefin alkylation reactor for use as catalyst. The trace amounts of light hydrocarbons and excess hydrogen can be used as refinery fuels or as feed for hydrogen production. The reaction products may also include a small amount of fluoride free residual which can be recovered for use as diesel fuel or heating oil. To minimize the residual oil formation, a hydrogenation catalyst may be used. Suitable metal components for the hydrogenation catalyst include Pt, Pd, Ni, W, NiW, NiMo, Mo, Co, and CoMo. Useful supports include active carbon, $Al_2O_3$, $SiO_2$, $TiO_2$, $ZrO_2$, silica-alumina, and zeolites. Useful combinations of metals on supports include $Pt/Al_2O_3$, Pd/C, $Pd/Al_2O_3$, $Ni/Al_2O_3$, $NiW/Al_2O_3$, $Mo/Al_2O_3$, $NiW/SiO_2Al_2O_3$, $NiMo/SiO_2Al_2O_3$, NiW/zeolite, and NiMo/zeolite.

Suitable hydrocracking catalysts include those solids commonly referred to as having medium or large pores which exhibit both acid and hydrogenation functions. The large pore size is preferred to enable the large polycyclic molecules to access the internal pore structure of the solid catalyst. Less specific cracking attributable to contact between the surface active sites and the ASO is also acceptable.

The acid function is predominately provided by the strong Bronsted acid present in the ASO (e.g., HF) but the presence of a solid catalyst acid function is nonetheless desirable to promote the cracking reaction. Such solid catalyst acid function is suitably provided either by an amorphous material such as alumina, silica-alumina, or silica, or by an aluminosilicate zeolite. Zeolites useful in the present invention are characterized by a Constraint Index of from less than about 1 up to about 12. Examples of which include mordenite, zeolite X, zeolite Y, ZSM-3, ZSM-18, or ZSM-20. The zeolites may be used in their various forms, for example, their cationic forms, preferably cationic forms of enhanced hydrothermal stability to resist the irreversible loss of the acid function upon exposure to the relatively severe hydrothermal conditions attendant to hydrocracking. For this reason, rare earth exchanged large pore zeolites such as REX and REY are preferred, as are ultra-stable zeolte Y (USY) and high silica zeolites such as dealuminized Y or dealuminized mordenite.

Zeolite ZSM-3 is taught in U.S. Pat. No. 3,415,736; zeolite ZSM-18 is taught in U.S. Pat. No. 3,950,496 and zeolite ZSM-20 is taught in U.S. Pat. No. 3,972,983. Each of these patents is incorporated by reference as if set forth at length herein for the details of the synthesis and properties of the respective zeolites.

Zeolite Beta which behaves as a large-pore or medium-pore zeolite under different process condition is also useful in the hydrocracking process of the present invention and is taught in U.S. Pat. Nos. 4,696,732; 3,308,069, as well as Re. 28,341, the entire contents of which are incorporated by reference as if set forth at length herein.

Examples of such zeolite catalysts also include the medium-pore zeolites (i.e., Constraint Index of from about 1 to about 12) such as ZSM-5, ZSM-11, ZSM-12, ZSM-22, ZSM-23, ZSM-35 and ZSM-48.

Zeolite ZSM-5 and the conventional preparation thereof are described in U.S. Pat. No. 3,702,886, the disclosure of which is incorporated herein by reference. Other preparations for ZSM-5 are described in U.S. Pat. Nos. Re. 29,948 (highly siliceous ZSM-5); 4,100,262 and 4,139,600, the disclosure of these is incorporated herein by reference. Zeolite ZSM-11 and the conventional preparation thereof are described in U.S. Pat. No. 3,709,979, the disclosure of which is incorporated herein by reference. Zeolite ZSM-12 and the conventional preparation thereof are described in U.S. Pat. No. 3,832,449, the disclosure of which is incorporated herein by reference. Zeolite ZSM-23 and the conventional preparation thereof are described in U.S. Pat. No. 4,076,842, the disclosure of which is incorporated herein by reference. Zeolite ZSM-35 and the conventional preparation thereof are described in U.S. Pat. No. 4,016,245, the disclosure of which is incorporated herein by reference. Another preparation of ZSM-35 is described in U.S. Pat. No. 4,107,195, the disclosure of which is incorporated herein by reference. ZSM-48 and the conventional preparation thereof is taught by U.S. Pat. No. 4,375,573, the disclosure of which is incorporated herein by reference.

Gallium-containing zeolite catalysts are useful in the present invention and are disclosed in U.S. Pat. Nos. 4,350,835 and 4,686,312, both of which are incorporated by reference as if set forth at length herein. The zinc-containing zeolite catalysts are similarly useful in the present invention. For example, U.S. Pat. Nos. 4,392,989 and 4,472,535 both teach zinc-containing zeolite catalysts and are incorporated by reference as if set forth at length herein. Catalysts such as ZSM-5 combined with a Group VIII metal described in U.S. Pat. No. 3,856,872, incorporated by reference as if set forth at length herein, are also useful in the present invention.

The method by which the Constraint Index is determined is described in U.S. Pat. No. 4,016,218, incorporated herein by reference for details of the method. U.S. Pat. No. 4,696,732 discloses Constraint Index values for typical zeolite materials and is incorporated by reference as if set forth at length herein.

The above-described Constraint Index provides a definition of those zeolites which are useful in the instant invention. The very nature of this parameter and the recited technique by which it is determined, however, admit of the possibility that a given zeolite can be tested under somewhat different conditions and thereby exhibit different Constraint Indices. Constraint Index seems to vary somewhat with severity of operations (conversion) and the presence or absence of binders. Likewise, other variables, such as crystal size of the zeolite, the presence of occluded contaminants, etc., may affect the Constraint Index. Therefore, it will be appreciated that it may be possible to so select test conditions, e.g. temperature, as to establish more than one value for the Constraint Index of a particular zeolite. This explains the range of Constraint Indices for some zeolites, such as ZSM-5, ZSM-11 and Beta.

It is to be realized that the above CI values typically characterize the specified zeolites, but that such are the cumulative result of several variables useful in the determination and calculation thereof. Thus, for a given zeolite exhibiting a CI value within a particular range, depending on the temperature employed during the the test method within the range of 290° C. to about 538° C., with accompanying conversion between 10% and 60%, the CI may vary within the indicated range. Likewise, other variables such as the crystal size of the zeolite, the presence of possibly occluded contaminants and binders intimately combined with the zeolite may affect the CI. It will accordingly be understood to those skilled in the art that the CI, as utilized herein, while affording a highly useful means for characterizing the zeolites of interest is approximate, taking into consideration the manner of its determination, with the possibility, in some instances, of compounding variable extremes.

Carbon supports are preferred in the present invention due to their ability to withstand the severe hydrothermal and corrosive environment of the ASO conversion reaction. Activated carbons are particularly preferred supports. Carbon supports become acidified in contact with the HF-containing ASO feed, and in their acidified state are effective ASO cracking catalysts.

The hydrogenation function is provided by a metal or combination of metals. Noble metals of Group VIIIA of the Periodic Table, especially platinum or palladium may be used, as may base metals of Groups IVA, VIA and VIIIA, expecially chromium, molybdenum, tungsten, cobalt and nickel. Combinations of metals such as nickel-molybdenum, cobalt-molybdenum, cobalt-nickel, nickel-tungsten, cobalt-nickel-molybdenum, and nickel-tungsten-titanium have also been shown to be effective.

In practicing conversion processes using the catalyst of the present invention, it may be useful to incorporate the above-described crystalline zeolites with a matrix comprising another material resistant to the temperature and other conditions employed in such processes. Such matrix materials include synthetic or naturally occurring substances as well as inorganic materials such as clay, silica and/or metal oxides. The latter may be either naturally occurring or in the form of gelatinous precipitates or gels including mixtures of silica and metal oxides. Naturally occurring clays which can be composited with the zeolite include those of the montmorillonite and kaolin families, which families include the sub-bentonites and the kaolins commonly known as Dixie, McNamee-Georgia and Florida clays or others in which the main mineral constitutent is halloysite, kaolinite, dickite, nacrite or anauxite. Such clays can be used in the raw state as originally mined or initially subjected to calcination, acid treatment or chemical modification.

In addition to the foregoing materials, the zeolites employed herein may be composited with a porous matrix material, such as alumina, silica-alumina, silica-magnesia, silica-zirconia, silica-thoria, silica-beryllia, and silica-titania, as well as ternary compositions, such as silica-alumina-thoria, silica-alumina-zirconia, silica-alumina-magnesia and silica-magnesia-zirconia. The matrix may be in the form of a cogel. The relative proportions of zeolite component and inorganic oxide gel matrix, on an anhydrous basis, may vary widely with the zeolite content ranging from between about 1 to about 99 percent by weight and more usually in the range of about 5 to about 80 percent by weight of the dry composite.

Additional catalyst modifying procedures which may also optionally be employed to modify catalyst activity or selectivity include precoking and presteaming (e.g., before oxide incorporation), or combinations thereof.

Upon heating and reaction, ASO becomes corrosive. Heater and reactor should be constructed from corrosion resistant materials. Laboratory experiments suggest that Hastelloy B or C and Monel would be acceptable materials of construction. For the low temperature equipment, Teflon R coated steel can be used.

To avoid coking in the fired heater, hydrogen gas or a hydrogen donor (such as hydrogen-rich i-$C_4$) may be added to the ASO stream before the stream enters the fired heater. The hydrogen addition rate typically falls within the range of from about 500 to about 2000 SCF/Bbl or more of ASO feed. Excess hydrogen is desirable to minimize coke formation, and the necessary hydrogen dosage will vary with the particular ASO feed. With a minimum of trial and error, the rate of hydrogen addition may be adjusted within the approximate range disclosed to prevent coking of the solid catalyst.

Useful hydrogen donors also include the light hydrocarbons such as the $C_1$–$C_5$ paraffins, as well as $C_5$+ naphthenes such as cyclopentane and cyclohexane.

BRIEF DESCRIPTION OF THE DRAWING

The Figure is a simplified schematic diagram showing initial processing steps in the method of the invention.

DESCRIPTION OF THE EMBODIMENT

Referring now to the Figure, the acid phase from the gravitation separator of a conventional HF alkylation process unit flows through line 10 to acid regenerator 20 where it is separated into an overhead stream 22 containing HF and alkylate and a bottom stream 24 containing ASO. Hydrogen or a hydrogen donor such as isobutane is optionally added as required via line 26 and the mixture enters fired heater 30 where it is heated to a temperature of about 200°–400° C. The heated mixture then flows through line 32 to reactor 40 (which may optionally contain a hydrogenation catalyst such as Pt/$Al_2O_3$) where the mixture liberates HF and converts to gasoline boiling range hydrocarbons including isoparaffinic alkylate. The HF and the gasoline boiling range hydrocarbons recycle to acid regenerator 20 via line 42.

The overhead stream 22 (containing HF and alkylate) from acid regenerator 20 flows to condenser/separator 50 where it separates into an overhead HF stream 52 and a bottom alkylate stream 54. The HF stream 52 is then recycled to the HF alkylation process unit (not shown) and the alkylate stream 54 is routed to product finishing and/or gasoline blending facilities (not shown).

Changes and modifications in the specifically described embodiments can be carried out without departing from the scope of the invention which is intended to be limited only by the scope of the appended claims.

What is claimed is:

1. A method for reclaiming HF and producing valuable gasoline blending components from acid soluble oils, ASO formed as a byproduct of acid-catalyzed isoparaffin-olefin alkylation, said method comprising the steps of:
   (a) reacting isoparaffin and olefin in the presence of a liquid acid alkylation catalyst to form alkylate and ASO byproduct;
   (b) separating alkylate, unreacted isoparaffin, and a majority of said liquid acid alkylation catalyst from said ASO;
   (c) mixing said ASO with a sufficient amount of hydrogen or a hydrogen donor to inhibit the reaction of ASO to coke at the elevated reaction temperature of step (d);
   (d) reacting said mixture of step (c) under conditions of elevated temperature and pressure to convert the hydrocarbon portion of said ASO to gasoline boiling range hydrocarbons and to liberate HF.

2. The process of claim 1 wherein said hydrogen donor is $H_2$.

3. The process of claim 1 wherein said hydrogen donor is a $C_1$–$C_5$ hydrocarbon.

4. The process of claim 3 wherein said hydrocarbon is a paraffin.

5. The process of claim 4 wherein said paraffin is isobutane.

6. The process of claim 1 wherein said hydrogen donor is a naphthene.

7. The process of claim 6 wherein said naphthene is cyclopentane or cyclohexane.

8. The process of claim 1 further comprising recycling liberated HF and gasoline boiling range hydrocarbons from step (d) to step (b).

9. The process of claim 1 further comprising recycling liberated HF and gasoline boiling range hydrocarbons from step (c) to step (a).

10. A method for reclaiming HF and producing valuable gasoline blending components from the ASO formed as byproduct of acid-catalyzed isoparaffin-olefin alkylation, said method comprising the steps of:

(a) reacting isoparaffin and olefin in the presence of a liquid acid alkylation catalyst to form alkylate and ASO byproduct;

(b) separating alkylate, unreacted isoparaffin, and a majority of said liquid acid alkylation catalyst from said ASO;

(c) mixing said ASO with a sufficient amount of hydrogen or a hydrogen donor to inhibit the reaction of ASO to coke at the elevated reaction temperature of step (d);

(d) reacting said mixture of step (c) under conditions of elevated temperature and pressure in the presence of a hydrogenation catalyst to convert the hydrocarbon portion of said ASO to gasoline boiling range hydrocarbons and to liberate HF.

11. The process of claim 10 wherein said hydrogen donor is $H_2$.

12. The process of claim 10 wherein said hydrogen donor is a $C_1$–$C_5$ hydrocarbon.

13. The process of claim 12 wherein said hydrocarbon is a paraffin.

14. The process of claim 13 wherein said paraffin is isobutane.

15. The process of claim 14 wherein said hydrogen donor is a naphthene.

16. The process of claim 15 wherein said naphthene is cyclopentane or cyclohexane.

17. The process of claim 10 further comprising recycling liberated HF and gasoline boiling range hydrocarbons from step (d) to step (b).

18. The process of claim 10 further comprising recycling liberated HF and gasoline boiling range hydrocarbons from step (c) to step (a).

* * * * *